(12) United States Patent
Davenport

(10) Patent No.: US 6,663,242 B1
(45) Date of Patent: Dec. 16, 2003

(54) SIMULTANEOUS, WAVELENGTH MULTIPLEXED VISION SCREENER

(76) Inventor: Wayne Davenport, 2223 Villaret Dr., Huntsville, AL (US) 35803

( * ) Notice: Subject to any disclaimer, the term of this patent is extended or adjusted under 35 U.S.C. 154(b) by 92 days.

(21) Appl. No.: 09/803,776

(22) Filed: Mar. 12, 2001

(51) Int. Cl.⁷ .................................. A61B 3/10
(52) U.S. Cl. ...................................... 351/221
(58) Field of Search ................. 351/205, 206, 351/208, 209, 210, 211, 221; 514/63

(56) References Cited

U.S. PATENT DOCUMENTS

| | | | |
|---|---|---|---|
| 3,806,725 A | 4/1974 | Leitz | 250/201 |
| 3,986,030 A | 10/1976 | Teltscher | 250/349 |
| 4,171,877 A | 10/1979 | Karasawa | 351/14 |
| 4,266,861 A | 5/1981 | Sawa | 351/7 |
| 4,305,398 A | 12/1981 | Sawa | 128/633 |
| 4,523,820 A | 6/1985 | Kaakinen | 351/206 |
| 4,586,796 A | 5/1986 | Molteno | 351/206 |
| 4,669,836 A | 6/1987 | Richardson | 351/206 |
| 4,717,952 A | 1/1988 | Kohayakawa | 358/113 |
| 4,834,528 A | 5/1989 | Howland | 351/211 |
| 4,836,670 A | 6/1989 | Hutchinson | 351/210 |
| 4,950,069 A | 8/1990 | Hutchinson | 351/210 |
| 4,989,968 A | 2/1991 | Freedman | 351/210 |
| 5,204,703 A | 4/1993 | Hutchinson | 351/210 |
| 5,218,387 A | 6/1993 | Ueno | 351/210 |
| 5,260,734 A | 11/1993 | Shindo | 354/219 |
| 5,280,313 A | 1/1994 | Kohayakawa | 351/211 |
| 5,355,895 A | 10/1994 | Hay | 128/745 |
| 5,502,520 A | 3/1996 | Cibis | 351/206 |
| 5,530,493 A | 6/1996 | Suzuki | 351/206 |
| 5,543,865 A | 8/1996 | Nanjo | 351/206 |
| 5,632,282 A | 5/1997 | Hay | 128/745 |
| 5,668,621 A | 9/1997 | Nanjo | 351/206 |
| 5,684,561 A | 11/1997 | Yancy | 351/209 |
| 5,953,100 A | 9/1999 | Sarver et al. | 351/206 |
| 5,989,194 A | 11/1999 | Davenport | 600/558 |
| 6,027,216 A | 2/2000 | Guyton | 351/200 |
| 6,089,715 A | 7/2000 | Hoover | 351/221 |
| 6,090,051 A | 7/2000 | Marshall | 600/558 |
| 6,095,989 A | 8/2000 | Hay | 600/558 |
| 6,440,950 B1 * | 8/2002 | Zeimer | 514/63 |

OTHER PUBLICATIONS

Simons, Kurt, PhD, Preschool Vision Screening: Rationale, Methodology and Outcome, Survey Of Ophthalmology, vol. 41, No. 1.

* cited by examiner

Primary Examiner—George Manuel
(74) Attorney, Agent, or Firm—Waddey & Patterson; Larry W. Brantley

(57) ABSTRACT

A method and apparatus for detecting refractive and non-refractive errors in a patient's eyes is disclosed. The apparatus includes an image-recording device for recording an image of the patient's eyes while illuminated with infrared light and while at least two different meridians of the patient's eyes are simultaneously illuminated with wavelength-encoded visible light. The apparatus further includes a wavelength-encoded light source for illuminating the patient's eyes with infrared light and at least two different meridians of the patient's eyes with wavelength-encoded visible light, and a control system for controlling the image-recording device and the light source. In one embodiment, the image-recording device includes a high-speed digital camera, the wavelength-encoded light source includes a group of infrared light-emitting diodes (LEDs) and a pair of wavelength-encoded flashes located in two different meridians of the camera, and the control system includes a computer system. In an alternative embodiment, the wavelength-encoded flashes are replaced with a wavelength-encoded ring flash.

50 Claims, 19 Drawing Sheets

FLASH #1

FLASH #2

First Order Approximation:

$\alpha = \tan^{-1}(x/y)$, y (nominally) = 12.5mm

SIMULTANEOUS, WAVELENGTH MULTIPLEXED VISION SCREENER

TECHNICAL FIELD

The present invention relates generally to a method and apparatus for screening a patient to detect diseases and abnormalities of the eyes and lids.

More particularly, this invention relates to a method and apparatus for photoscreening a patient by generating wavelength-encoded images of a patient's eyes and analyzing these images to detect diseases and other abnormalities.

BACKGROUND OF THE INVENTION

It is well known that approximately 2–5% of children will develop some degree of amblyopia and another 15%–20% possess some form of visual malady. Screening eyes to detect diseases and abnormalities, such as refractive errors, both spherical and cylindrical in optical power, ocular alignment, media opacities, and ptosis, is very important because if these diseases are not corrected before the ages of 7 to 9, a person may suffer irreversible vision loss. Screening eyes in young children accurately and consistently, however, is not an easy task, especially when computer automated diagnosis in involved.

As mentioned previously, many of these diseases and abnormalities must be detected and corrected at an early age, and, accordingly, the typical screening patient is a child in preschool through third grade. Generally, patients in this age group have a very short attention span, which makes it difficult to perform an accurate screening of the eye. As a result, screening tests for patients in this age group must be expeditious, simple, passive (i.e., no patient-technician interaction), non-intrusive, and portable enough for field-testing in the school environment. One type of screening test that satisfies these criteria is photoscreening.

Photoscreening is the process of taking a photograph of the patient's eyes and analyzing that photograph to detect diseases and other abnormalities. In general photoscreening systems include a camera (film or digital), and single, multiple, or ring-type flashes located near (or on) the camera's optical axis. By simultaneously illuminating the eyes with the flash and taking a photograph, one creates an image that may be analyzed to detect diseases and other abnormalities in the eyes.

It is known in the art that Caucasians produce a distinctive red retinal reflex, or retinal return reflection in a photo-screened image. This red retinal reflection is visible to the camera when illuminated by a near (or on) axis flash and the pupils are sufficiently dilated. Other ethnic groups, however, differ rather dramatically. Persons from African-American, Asian, and Hispanic descent do not, in general, produce a red retinal reflex and, in fact, with an eye that can focus properly, off axis photoscreening may produce no detectable retinal reflex. This is particularly alarming since it may be difficult, if not impossible, to detect cataracts or other media opacities in these ethnic groups via traditional photoscreening techniques. The present invention overcomes the deficiencies associated with traditional photoscreening and allows a robust method for computer-aided screening.

For example, U.S. Pat. No. 5,989,194 issued to Davenport et al. on Nov. 23, 1999 and entitled, "Method and Apparatus for Detecting Ocular Disease and Abnormalities" and U.S. Pat. No. 6,095,989 issued to Hay et al. on Aug. 1, 2000 and entitled, "Optical recognition methods for locating eyes" (continuation-in-part of U.S. Pat. Nos. 5,632,282 and 5,355,895.) both teach a screening system which includes a singular flash and provides information in only one meridian of the eye. As a result, these systems are unable to detect astigmatism in some axes of the eye and, in addition, neither of these patents allows one to obtain quantitative numbers relating to the patient's pupil size or baseline retinal reflectivity prior to the actual photoscreening process. It should also be noted that the Hay patent includes extensive techniques for computer analysis of typical photoscreened images and, therefore, has inherent difficulties analyzing these images on the minority groups mentioned earlier. The contention is that robust analysis of traditional (single, double, or ring type off-axis flash systems) photoscreened images for media opacities and refractive errors is difficult to perform, and is especially difficult to analyze via computer image processing. The present invention, with its novel infrared prescreening capabilities and wavelength encoded image acquisition, allows for robust image analyses across all ethnic groups by both manual and digital means.

A two-flash screening system is described in U.S. Pat. No. 4,523,820 issued to Kaakinen on Jun. 18, 1985, and entitled "Procedure and Means for Establishing and Recording Errors of the Eye". The '820 patent teaches a system and method for obtaining a photograph of a patient's eyes by simultaneously triggering two flashes located in different meridians of the eye. It is true that this system is more robust in the detection of astigmatism over single flash systems, but, because both flashes are triggered simultaneously and overlap in the resulting photograph, it is difficult to interpret the contributions made from each flash. While it may be possible to determine that a patient's vision has sphere and cylinder errors, the overlapped images make it difficult to specify the extent of these errors. This system also suffers from problems associated with traditional photoscreening systems mentioned earlier.

Additional two-flash photoscreening systems are described in U.S. Pat. No. 4,989,968 issued to Friedman on Feb. 5, 1991 and entitled, "Photoscreening Camera System" and U.S. Pat. No. 6,089,715 issued to Hoover et al. on Jul. 18, 2000 and entitled "Automated Photo refractive Screening". Both of these patents describe systems that are similar to the ones in the '820 patent, except that the flashes are either mechanically rotated or the camera is physically rotated in order to get two singular photographs, each containing information regarding different meridians of the eye. The primary problem with both of these systems is the 15 to 20 second time delay between the flashes. During this time delay, the patient's pupils may change in diameter, the eyes may change in accommodation, or the eyes may align differently, any of which will cause a significant increase in false positive screenings. Again, both of these systems suffer from problems associated with traditional photoscreening systems mentioned earlier. It should be noted that the algorithms employed by the Hoover patent base their pupil detection on the red retinal reflex (step 52 '715 patent) in order to perform computer-aided diagnosis.

Finally, a screening system utilizing a ring flash is disclosed in U.S. Pat. No. 4,586,796 issued to Molteno on May 6, 1986 and entitled, "Testing to Determine the Fixation and Focusing of Living Eyes". While this system does allow one to determine that there is a problem with the eyes, determining the type of problem is difficult. This is true because the ring flash is symmetrical around the optical axis and, as a result, while it is possible to detect both cylindrical and spherical optical errors, it is unclear in the photograph whether the spherical error is myopic or hyperopic in nature or in which axis the cylinder power is oriented.

Thus, what is needed is a robust system and method for screening eyes that allows one to detect and identify various types of diseases and abnormalities in the eyes with a high degree of accuracy and specificity across all ethnic groups.

SUMMARY OF THE INVENTION

The present invention provides an apparatus and method for generating 1.) infrared illuminated images, and 2.) wavelength-encoded images (i.e., the images are generated using different wavelengths of light) of a patient's eyes and 3.) analyzing these images to detect diseases and abnormalities.

The apparatus includes a device for recording images of a patient's eyes while 1.) the eyes are being illuminated with infrared light, and 2.) the eyes are being simultaneously illuminated with wavelength-encoded light in at least two different meridians of the eyes. The apparatus also includes a light source for 1.) illuminating the patient's eyes with infrared light, and 2.) for illuminating the patient's eyes with wavelength encoded light. Finally, the apparatus includes a system for controlling both the image-recording device and the wavelength encoded light sources.

The method includes the steps of illuminating and recording images of the patient's eyes with infrared light. These infrared images are used to determine the pupil size, baseline retinal reflectivity, and to identify non-refractive errors, such as cataracts, esotropia, and exotropia. These steps are immediately followed by the simultaneous triggering of multiple, wavelength encoded light sources, in at least two different meridians of the patient's eyes. These wavelength-encoded images are used to identify refractive errors, such as astigmatism, myopia, and hyperopia. In addition, by capturing the images simultaneously, the present invention eliminates errors caused by changes in dilation, accommodation, or alignment. Furthermore, the decoding step eliminates the overlapping information problem created by the '820 patent by separating the wavelength-encoded image into two wavelength-decoded images, each containing an image of the patient's eyes generated by a different color of light.

In one embodiment, the image-recording device includes a high-speed digital camera, the infrared light source includes a plurality of infrared light-emitting diodes (LEDs), the wavelength encoded light sources include a pair of commercially available off-the-shelf flashes commonly used with cameras, and the control system includes a computer system. The high-speed digital camera, which normally includes an infrared filter, is made sensitive to infrared light by removing the filter. This allows the camera to record both visible and infrared images. Each of the flashes includes two filters, one encoded and operable to pass only one color of light (red or green), and a second encoded to block infrared light. The infrared filter is used so each flash will emit only one color and facilitate subsequent decoding. In an alternative embodiment, the light source includes a ring flash with one wavelength encoded filter covering one meridian of the ring flash, a second wavelength encoded filter covering a second meridian of the ring flash, and the remainder of the ring flash covered by a filter that blocks all light generated by the remainder of the ring flash. In both embodiments the computer system controls the camera and the flashes (or flash in the case of the ring flash). In addition, the computer system decodes the wavelength-encoded image of the patient's eyes into wavelength-decoded images and analyzes the infrared and decoded images to determine pupil size, non-refractive errors, and refractive errors.

DESCRIPTION OF THE PREFERRED EMBODIMENTS

Figure 1:
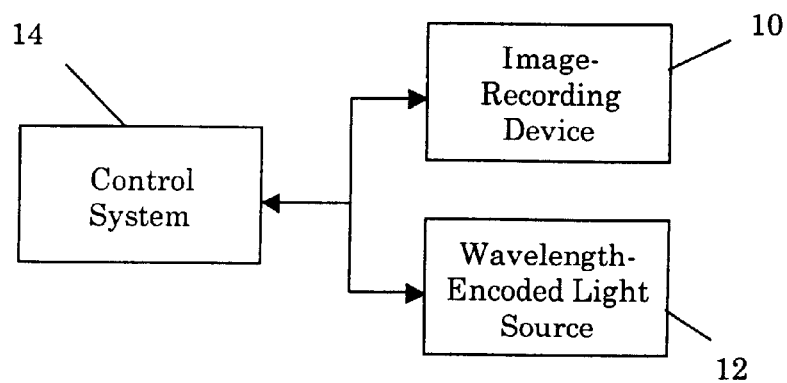
FIG. 1 is a block diagram of one embodiment of the present invention.

Referring to FIG. 1, the present invention includes an image-recording device 10, a wavelength-encoded light source 12, and a control system 14.

The image-recording device 10 is operable to record images of a patient's eyes 1.) while illuminated by infrared light and 2.) while being illuminated by simultaneous wavelength-encoded visible light in least two different meridians of the patient's eye's.

The wavelength-encoded light source 12 is operable to 1.) illuminate the patient's eyes with infrared light and to 2.) simultaneously illuminate at least two meridians of the patient's eyes, each with independent, wavelength-encoded visible light. In other words, the light source 12 is operable to illuminate the patient's eyes with infrared light, one meridian of the patient's eyes with one color of light, and a second meridian of the patient's eyes with a second color of light. In addition, while the discussion of the present invention that follows refers to a system that illuminates two different meridians of the patient's eyes, alternative embodiments might simultaneously illuminate more than two meridians of the patient's eyes.

The control system 14 communicates with and controls both the image-recording device 10 and the light source 12. Specifically, the control system 14 is operable to cause the light source 12 to generate infrared light and wavelength-encoded visible light in two different meridians of the patient's eyes. It subsequently causes the recording device 10 to record images of the patient's eyes while being illuminated by the visible/infrared light sources. In addition, the control system 14 decodes the wavelength-encoded images of the patient's eyes into two wavelength-decoded images, and analyzes the infrared and decoded images to determine pupil size, base-line reflectivity, non-refractive errors, and refractive errors.

Figure 2:
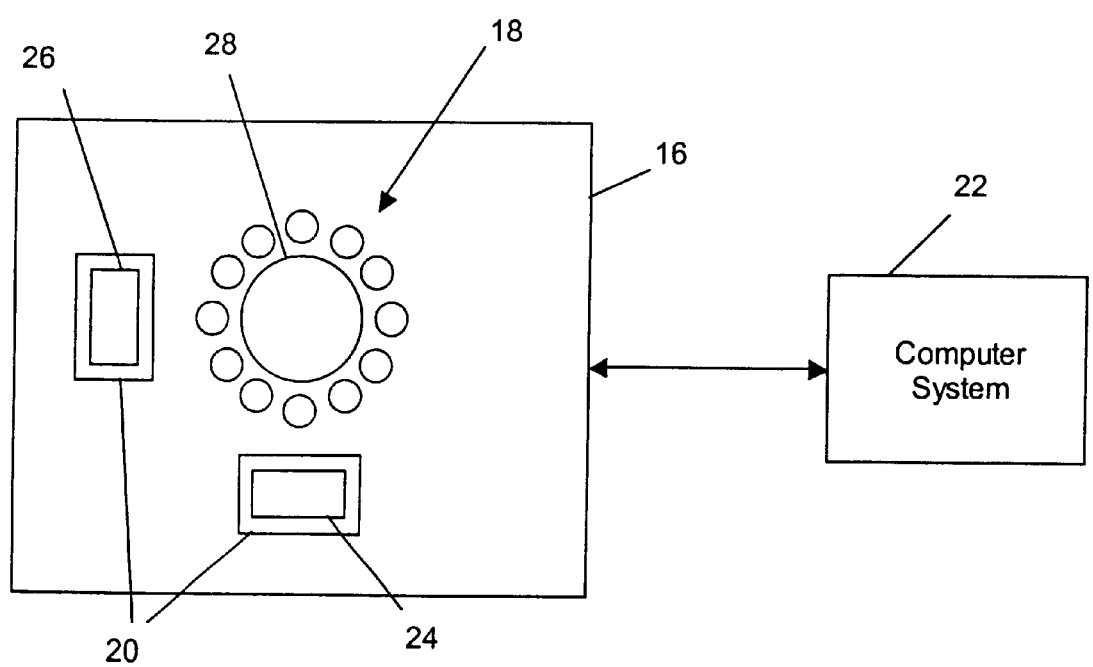
FIG. 2 is a sketch diagram of a second embodiment of the present invention.

Referring to FIG. 2, in one embodiment of the present invention the image-recording device 10 includes a high-speed digital camera 16, the wavelength-encoded light source 12 includes a plurality of infrared light-emitting diodes (LEDs) 18 and a pair of wavelength-encoded flashes 20 that are located in two different meridians of the camera's optical axis. The control system 14 includes a computer system 22, which is connected to the camera 16, the LEDs 18, and the pair of flashes 20. Also included in control system 14 is a monitor (not shown), for displaying infrared and wavelength-encoded/decoded images of the patient's eyes.

Figure 3:
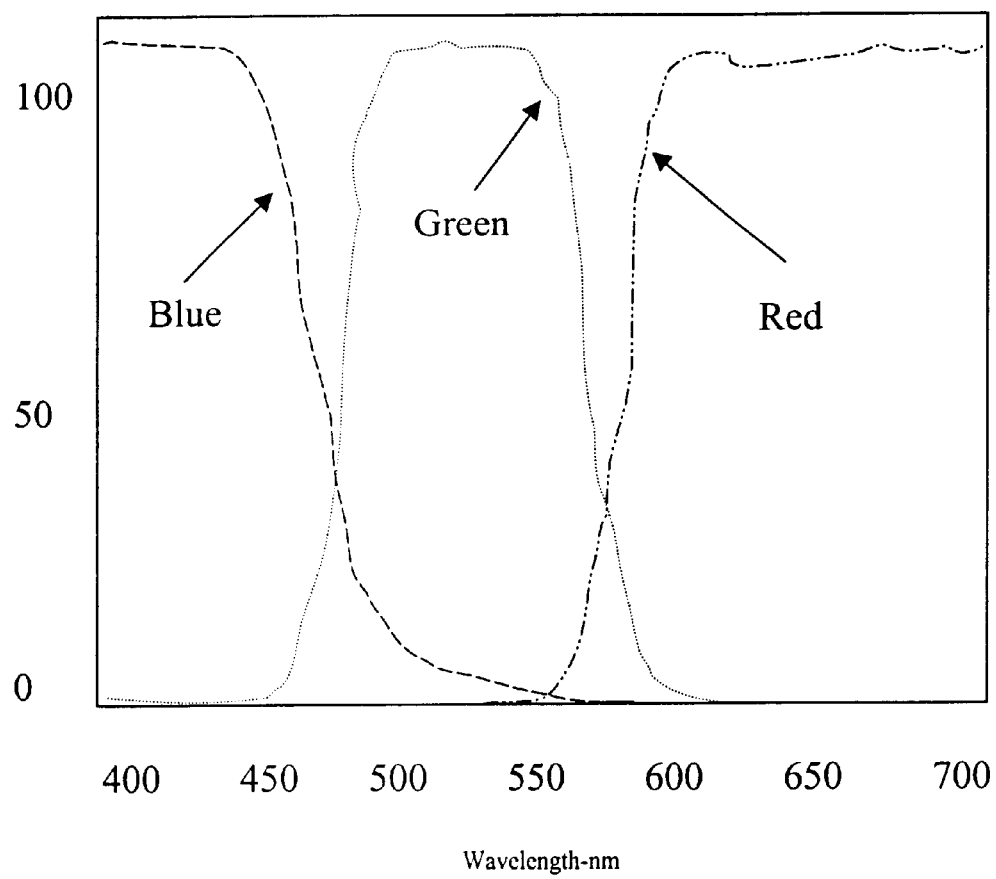
FIG. 3 is a plot showing the pixel sensitivity of the digital camera shown in FIG. 2.

The camera 16 includes a sensor (not shown) having a large number of color sensitive pixels (not shown). These pixels are sensitive to only red, green, or blue wavelengths and record intensity values of light having some combination of these wavelengths. For example, a scene that contains only red would only be recorded as an intensity value by the red sensitive pixels, and consequently, the green and blue pixels would have an effective intensity value of zero. FIG. 3 is a plot of the pixel sensitivity of the camera 16. In addition, the infrared filter (not shown) built into the camera 16 is removed so that the camera 16 can record infrared images of the patient's eyes.

Figure 4:
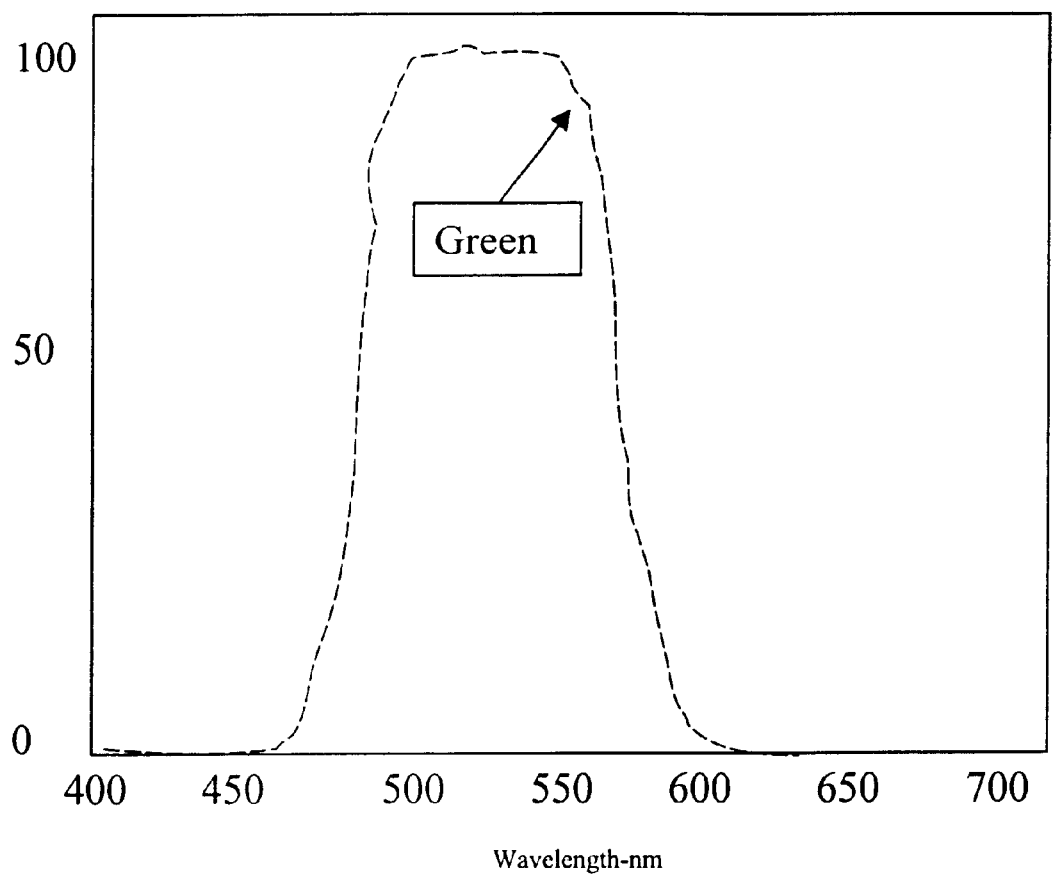
FIG. 4 is a plot showing the filter characteristics of one wavelength-encoded filter used in the present invention.
Figure 5:
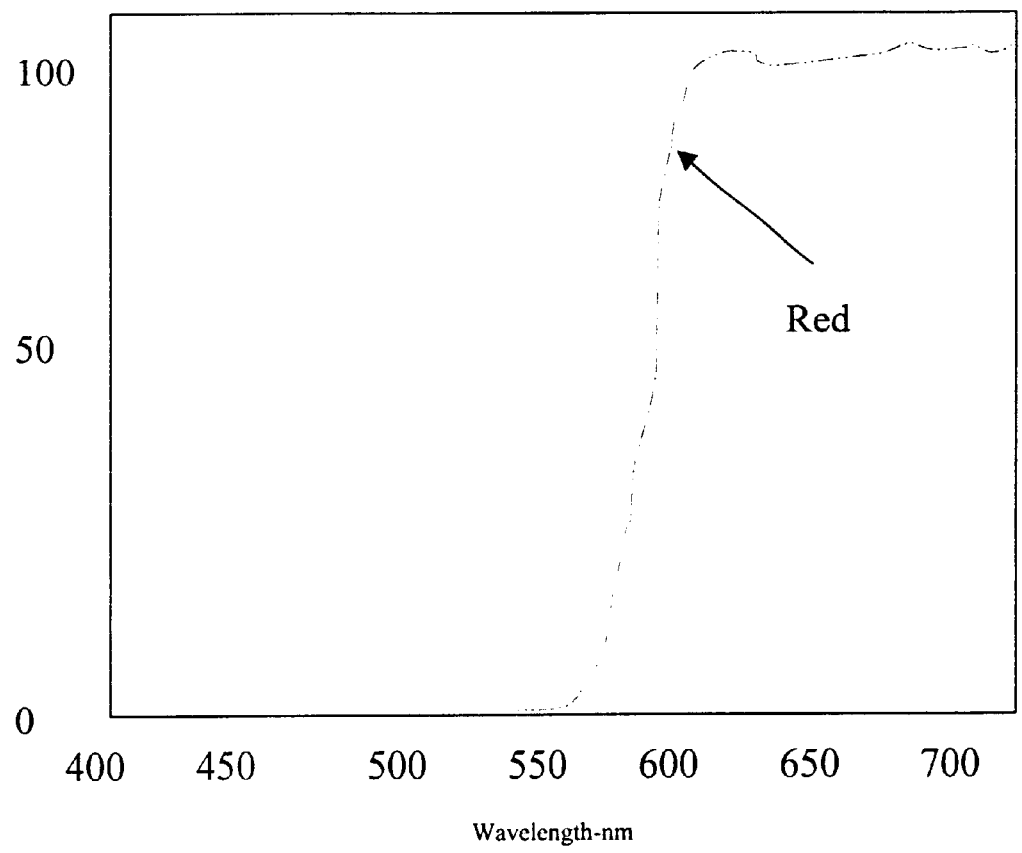
FIG. 5 is a plot showing the filter characteristics of a second wavelength-encoded filter used in the present invention.

Wavelength-encoded flashes 20 include wavelength-encoded filters, 24 and 26, for generating wavelength-encoded light. In one embodiment, filter 24 filters out light having wavelengths that are not included in the range of wavelengths commonly referred to as the color green and filter 26 filters out light having wavelengths that are outside of the range of wavelengths commonly referred to as the color red. As a result, when the wavelength-encoded flashes 20 are triggered, filter 24 emits green colored light and filter 26 emits red colored light. The filter characteristics of the filters, 24 and 26, are shown in FIGS. 4 and 5, respectively. As shown in FIG. 4, green filter 24 only passes light having wavelengths ranging from approximately 470 nanometers to approximately 550 nanometers at full width half maximum (FWHM). As shown in FIG. 5, red filter 26 passes light having wavelengths greater than 600 nanometers FWHM. Both flashes also have a filter that blocks the infrared above 700 nm.

Figure 6:
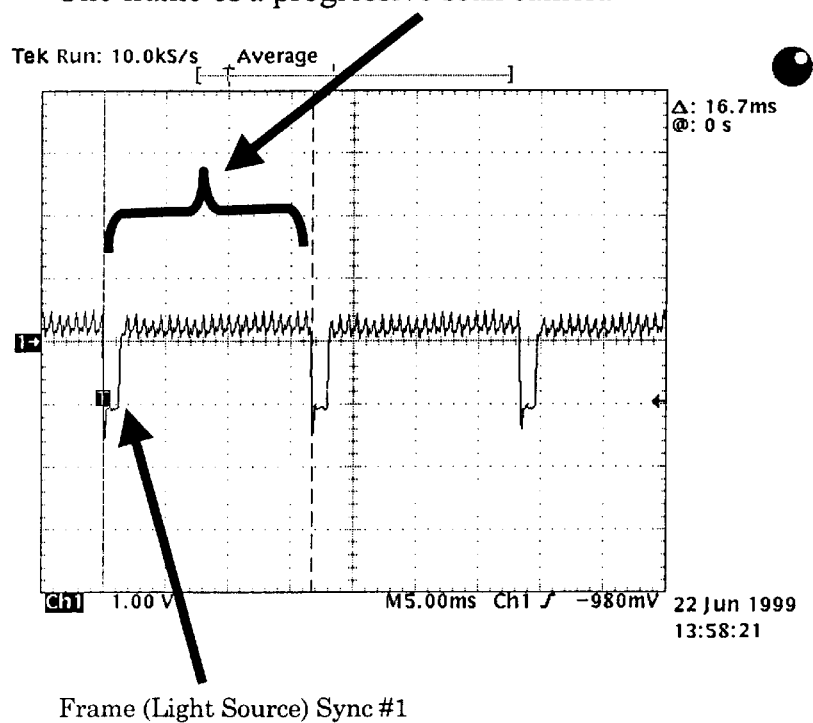
FIG. 6 is a plot of an output signal from the digital camera shown in FIG. 2 that is used to control the simultaneous triggering of the flashes.

In this embodiment, the high-speed, digital, color, camera 16 in FIG. 2 is a Vitana PL-A634 Color CMOS camera with 1280×1024 (programmable) resolution and includes horizontal, vertical, and strobe output syncs (not shown) and the wavelength-encoded flashes 20 are triggered based on the strobe output sync of the camera 16, which is shown in FIG. 6.

The LEDs 18 are manufactured by Photonic Detectors (part no. PDI-E803), the flashes 20 are Vivitar model 283, and the wavelength-encoded filters, 24 and 26, are color dichroic filters available in various sizes from Edmund Scientific. The infrared block filter (not shown) is Schott KG-3 glass. Finally, the computer 22 is a Dell Pentium 3 computer system using an Intel Pentium 3 processor.

The camera 16 includes a Nikon 100 mm objective lens 28. Since typical photographic lens do not maintain sharp focus from the visible to the near infrared, the objective lens 28 must be adjusted when capturing images of the patient's eyes while being illuminated by infrared light and then while illuminated by wavelength-encoded visible light. The adjustment (refocusing) to the objective lens 28 may be performed manually or using an adjustment mechanism (not shown), such as a stepper motor. In an effort to alleviate the refocusing problem, an alternative embodiment utilizes an objective lens 28 that is custom designed for focusing light having wavelengths ranging from 500 nanometers to 950 nanometers.

The adjustment to the camera's shutter speed may be controlled by the control system 14. In one embodiment, the shutter speed is set to $1/30^{th}$ of a second for recording infrared images and $1/500^{th}$ of a second for recording the wavelength-encoded images. The shutter speed of $1/500^{th}$ of a second is approximately the flash duration time and is used to ensure underexposure of the infrared light (i.e., the exposure is not long enough for the infrared light to register on the wavelength-encoded image). This is desirable because infrared light is not wanted in the exposure since the wavelength-encoded image is to be used for refractive error determination.

In another embodiment, the present invention includes several small flashing LEDs (not shown) placed near the camera's objective lens 28 to get the attention of the patient and to allow the patient to focus his/her eyes at the proper distance for accurate refractive screening. Although this embodiment uses flashing LEDs, other types of devices may also be included in the present invention to get the attention of the patient.

Although the present invention is described in FIG. 2 as having a light source 12 that includes an infrared light source, such as infrared LEDs 18, the inventor of the present invention also contemplates a system that does not include the LEDs 18. In such an embodiment, the infrared filter (not shown) of camera 16 does not have to be removed.

Figure 7:
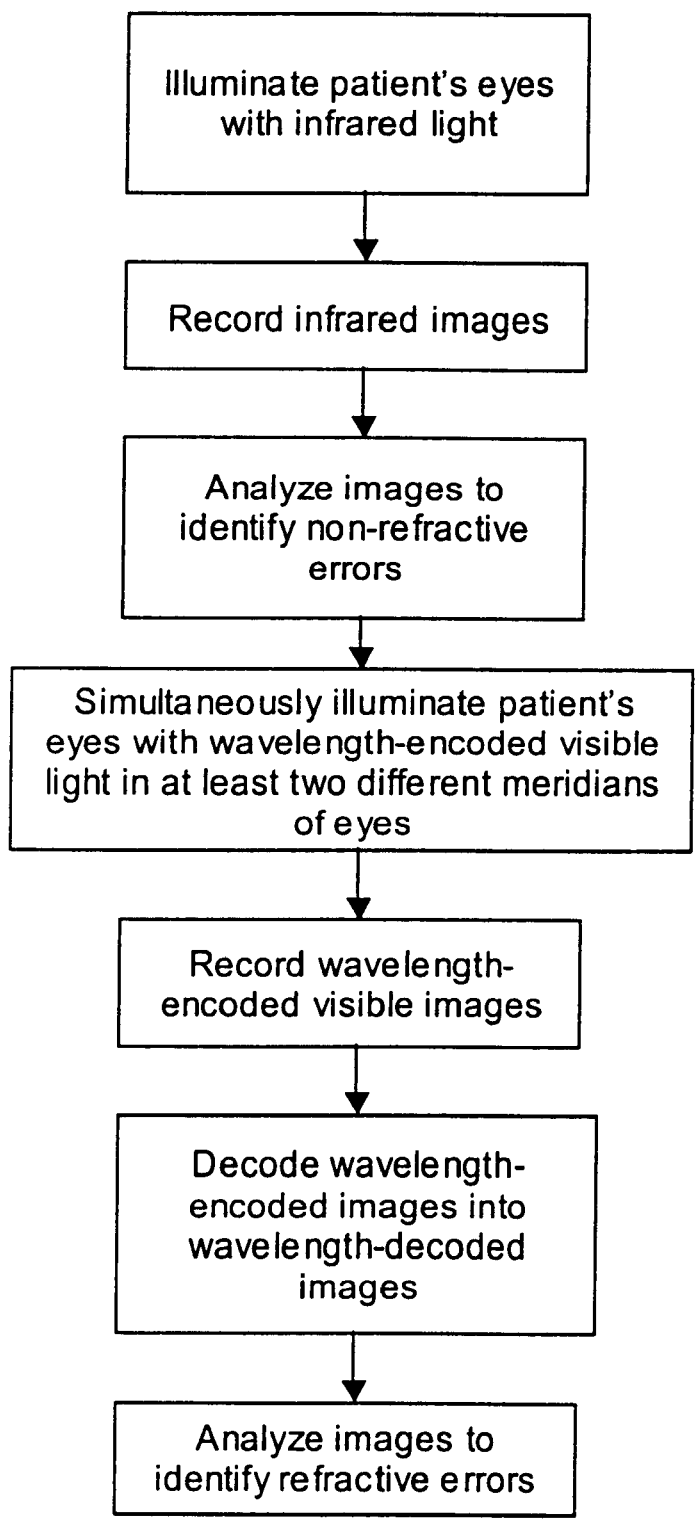
FIG. 7 is a flowchart showing the method steps included in the present invention.
Figure 8:
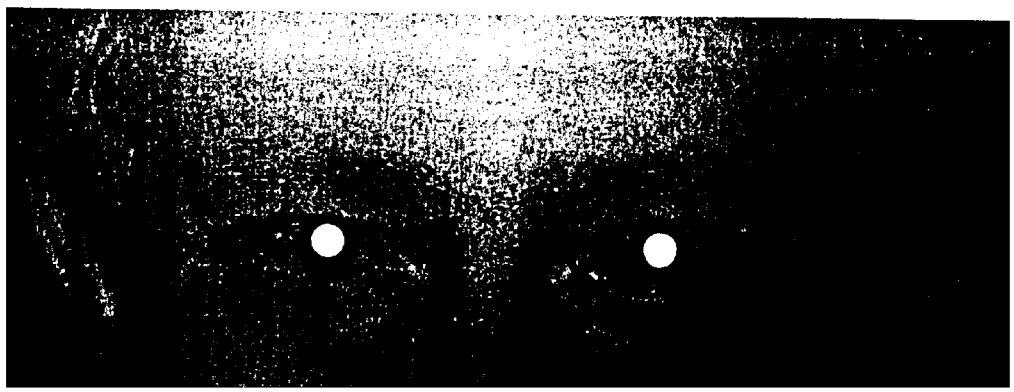
FIG. 8 is an image showing a patient's eyes illuminated by infrared light and the resulting corneal reflections and complete pupil flooding.

Referring to FIG. 7, the method disclosed in the present invention includes the steps of illuminating the patient's eyes with infrared light using the wavelength-encoded light source 12, recording images of the patient's eyes while illuminated with infrared light, and analyzing the resulting infrared images to identify non-refractive errors, such as media opacities (cataracts) and strabismus (esotropia, exotropia). A typical resulting infrared image is shown in FIG. 8.

Cataracts may be identified by reviewing an infrared image of the patient's eyes and detecting the dark areas. Note that the image of the eyes shown in FIG. 8 does not include any dark spots and accordingly, this patient did not have cataracts at the time the image was recorded.

Figure 9:
FIG. 9 is a drawing showing a patient's eyes illuminated with infrared light and indicating esotropia.
Figure 10:
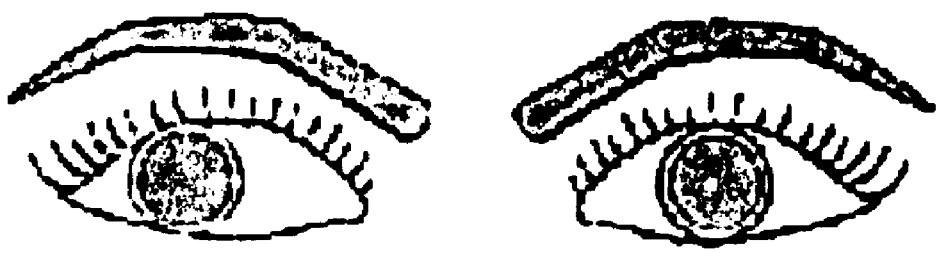
FIG. 10 is a drawing showing a patient's eyes illuminated with infrared light and indicating exotropia.

Strabismus, i.e., esotropia (eye turned toward nose) and exotropia (eye turned toward temple), may also be detected by reviewing the infrared images of a patient's eyes. Specifically, strabismus may be detected by reviewing the infrared image and calculating the gaze angle of the eyes. Gaze angle is performed by locating the reflection of the light source 12 off of the cornea (the outer surface of the eye) and comparing that to the X-Y center of the pupil. As shown in FIG. 8, this reflection appears as a bright spot in the image near the center of the patient's eyes. FIGS. 9 and 10 show drawings of a patient's eyes indicating exotropia and esotropia, respectively.

Finally, the infrared images may also be used to determine pupil size, which is an important metric in photoscreening. If the eyes are not dilated at least 5 millimeters, then an insufficient amount of light enters the patient's pupil and it is difficult to obtain an accurate screening. In an addition to the insufficient light, optical properties of small apertures may cause the eyes to appear in correct focus to a photo-screening device. In any event, the analysis to detect cataracts, strabismus, baseline retinal reflectivity, and pupil size may be performed manually (by a person reviewing the infrared images of the patient's eyes) or by using a computer. In one embodiment of the present invention, the computer 22 is operable to analyze the infrared images to determine these conditions. In this embodiment, the computer system 22 analyzes the infrared images by performing the steps shown in FIG. 11.

Figure 11:
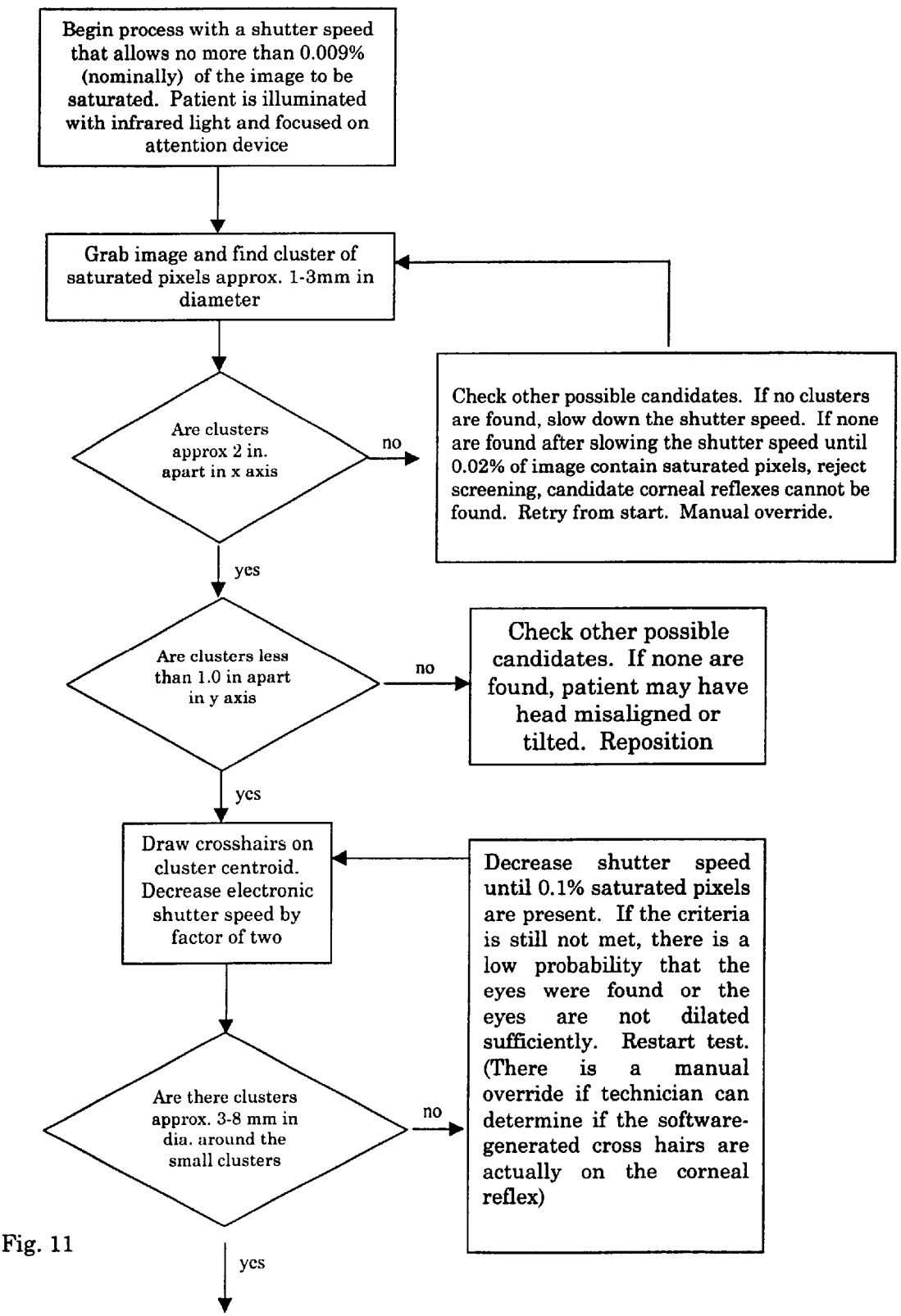
FIG. 11 is a flow chart showing the steps performed by the computer system to analyze infrared and visible light images of a patient's eyes.
Figure 11:
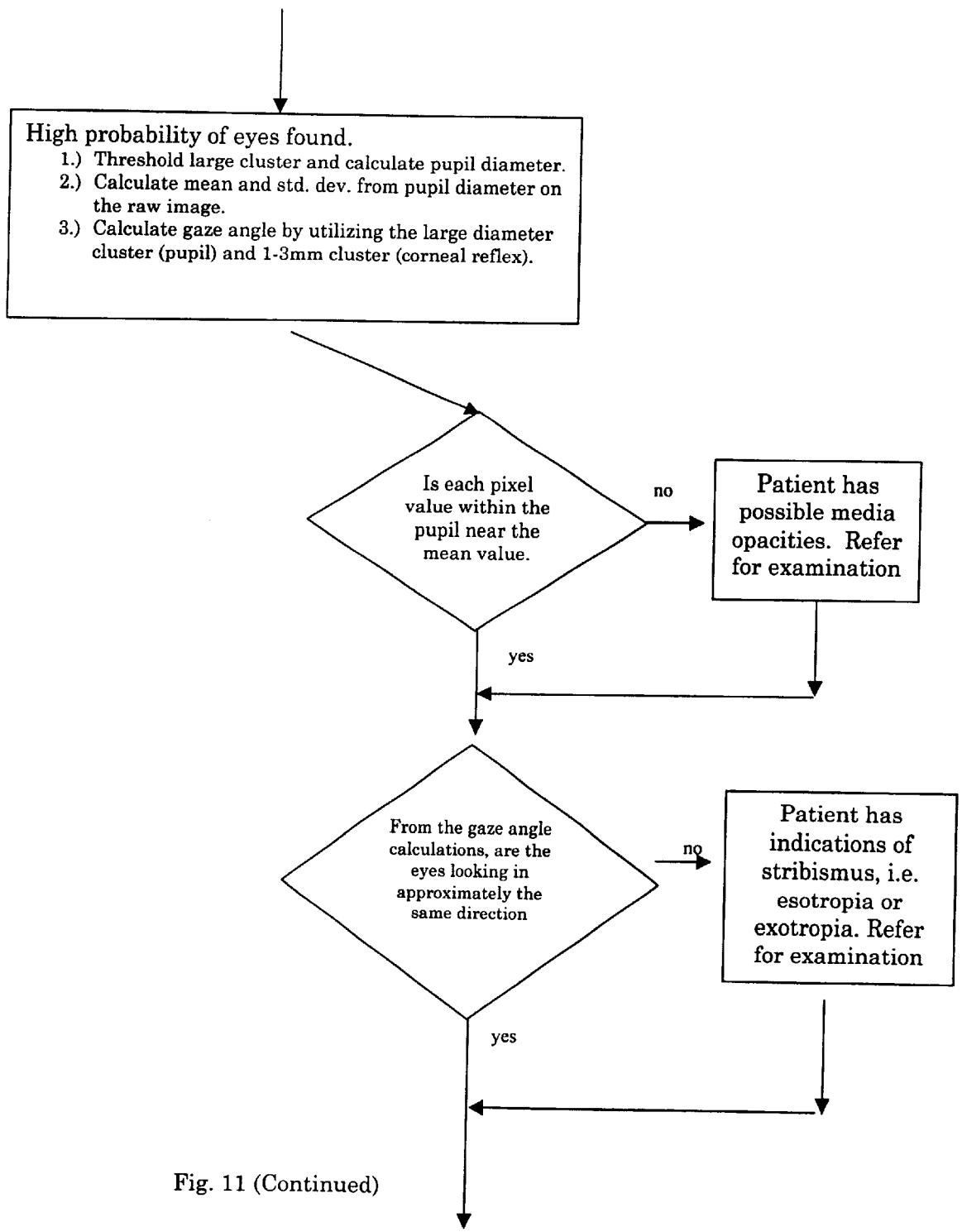
Figure 11:
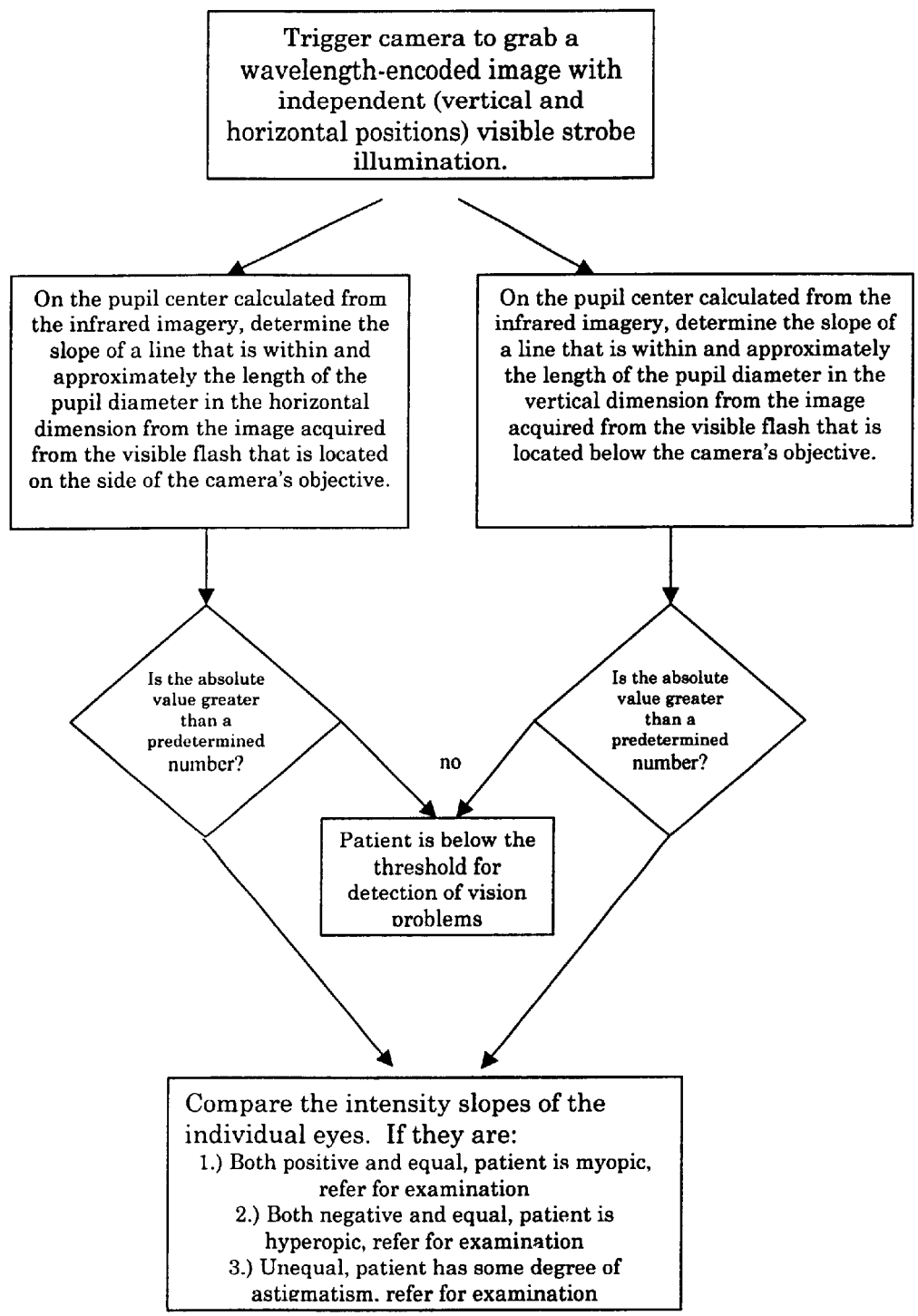

Referring to FIG. 11, the computer system 22 locates the patient's eyes in the infrared image. This is accomplished by searching the infrared images for first surface reflections, which typically will include 3–4 saturated pixels (approximately 1 mm in diameter). Once the saturated pixels are located, the computer system 22 determines if two sets of saturated pixels are separated by approximately 2 inches along the x-axis. If the two sets are not separated by approximately 2 inches, the computer system 22 searches for additional sets of saturated pixels. If no additional sets are found, the computer system 22 decreases the shutter speed in order to locate additional sets of saturated pixels. If the shutter speed is decreased to the point that 0.02% of the image contains saturated pixels and the above criteria is not satisfied, the computer system 22 determines that the eyes cannot be found. At this point, a technician operating the computer system 22 can manually override the computer system 22 and proceed to the next step.

The candidate pixels found that fit the above x-axis criteria are then subjected to tests to determine if they are aligned along the y-axis. If a pair of the candidate pixels are located within approximately 1.0 inch of each other along the y-axis, then the criteria is assumed met, and the screening process continues. However, if none are found, the computer system 22 does not continue the screening of the infrared image and provides an indication to a technician operating the computer system 22 that there is not a high level of confidence that the patient's eyes have been found. In this case, the patient may have his/her head misaligned or tilted, the technician can reposition the patient, and the technician can restart the search process. In addition, the technician can manually override the computer system 22 and proceed to the next step.

Next, the computer system 22 determines if the pair of first surface reflections are surrounded by a "circle" or "cluster" (which is most likely the pupil of the eye) of approximately 10 to 50 illuminated pixels (approximately 3–8 mm) in diameter. To do this, the computer system 22 draws crosshairs on the pair of saturated pixels deemed to be the corneal reflex and decreases the shutter speed by approximately a factor of two and searches the resulting image for the "circles." If the "circles" are not found, the computer system 22 decreases the shutter speed until approximately 2–5% of the infrared image contains saturated pixels. If the "circles" still cannot be found, the computer system 22 determines that the eyes were not found and restarts the search process. A technician can override the computer system 22 and proceed to the next step since he or she can determine that the crosshairs are actually positioned on the patient's corneal reflex.

Next, the computer system 22 calculates the pupil diameter using the "circles" and thresholding the image. If the patient's eyes are not dilated 5 millimeters or more, the computer system 22 provides an indication of that fact to the operator of the present invention. The amount of eye dilation determines the confidence level that is attached to conclusions drawn by analyzing the infrared images. For example, if the patient's eyes are dilated less than 5 mm, then the confidence level associated with the refractive error screening is low for reasons mentioned earlier.

Next, the computer system 22 looks for media opacities, such as cataracts, by measuring the intensity of the light of the infrared image of the patient's eyes on a pixel-by-pixel basis. This is accomplished by calculating the illumination mean of the "circle" area referenced above using the raw infrared image. If an area of the patient's eyes includes a decreased level of infrared light, the computer system 22 determines that media opacities, such as a cataract, may be present in the patient's eyes and provides an indication of that fact to the technician.

Finally, the computer system 22 determines the gaze angle of the patient's eyes, and, in turn, if the patient has esotropia or exotropia. This is accomplished by calculating the distance between the corneal reflection and the geometrical center of each pupil. To illustrate, consider FIG. 12.

Figure 12:
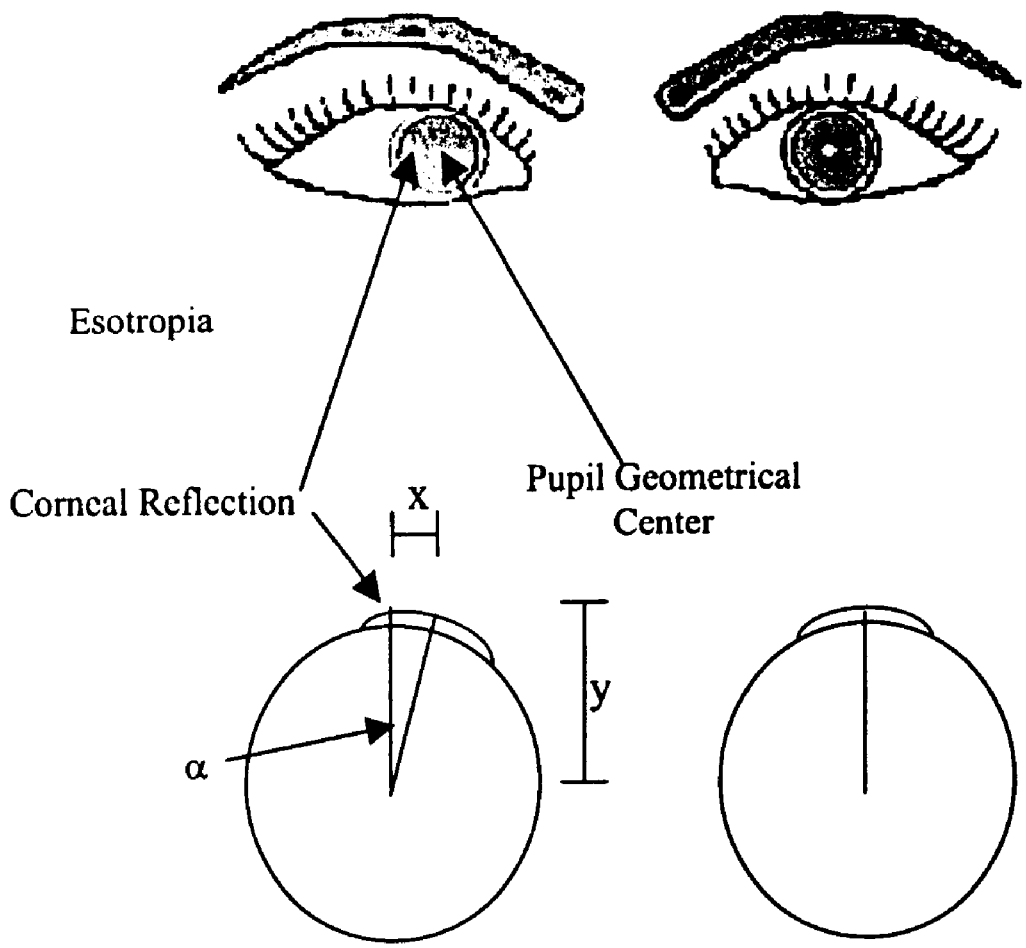
FIG. 12 is a drawing showing a front view and top view of a patient with exotropia.

FIG. 12 includes a front view and a top view of a pairs of eyes having esotropia, the right eye being aligned correctly and the left eye being misaligned. The front views include white dots in the pupil labeled "corneal reflection" and cross hair center points labeled "pupil geometrical center." The top view also includes points that correspond to the location of the corneal reflections and the geometric centers, and are labeled accordingly.

Referring to the right top view, the corneal reflection point and the cross hair center point are located approximately at the same position, indicating that the eye is aligned correctly. In the left top view, however, the corneal reflection point and the cross hair center point are not located in approximately the same position and this indicates that the eye is misaligned. The computer system 22 calculates the distance between the corneal reflection point and the cross hair center point and expresses this distance as an angle, $\alpha$. This angle $\alpha$ is referred to as the gaze angle of the eyes and is used to determine if the eyes are misaligned. If the gaze angle is approximately zero, then a patient does not have an alignment problem. If, on the other hand, the gaze angle is non-zero, then the patient may have an alignment problem.

In one embodiment, the gaze angle, $\alpha$, is calculated using the distance between the corneal reflection and the cross hair center point of each eye, labeled as the x distance, and the distance between the center of the eye and the cross hair center point, labeled as the y distance (this distance is usually approximately 12.5 mm, but it may vary from person to person). A first order approximation of the gaze angle is then calculated by taking the inverse tangent of the ratio of the x distance over the y distance. In other embodiments, however, other types of approximations may be used as well.

Returning to FIG. 7, the method disclosed in the present invention further includes the steps of simultaneously illuminating two different meridians of the patient's eyes with wavelength-encoded light, recording an image of the patient's eyes while illuminated with the wavelength-encoded light, decoding the wavelength-encoded image into a pair of wavelength-decoded images, and analyzing the resulting wavelength-decoded images to identify refractive errors in the patient's eyes. Typical wavelength-encoded and wavelength-decoded images of a patient's eyes with various refractive errors are shown in FIGS. 13–18.

Figure 13:
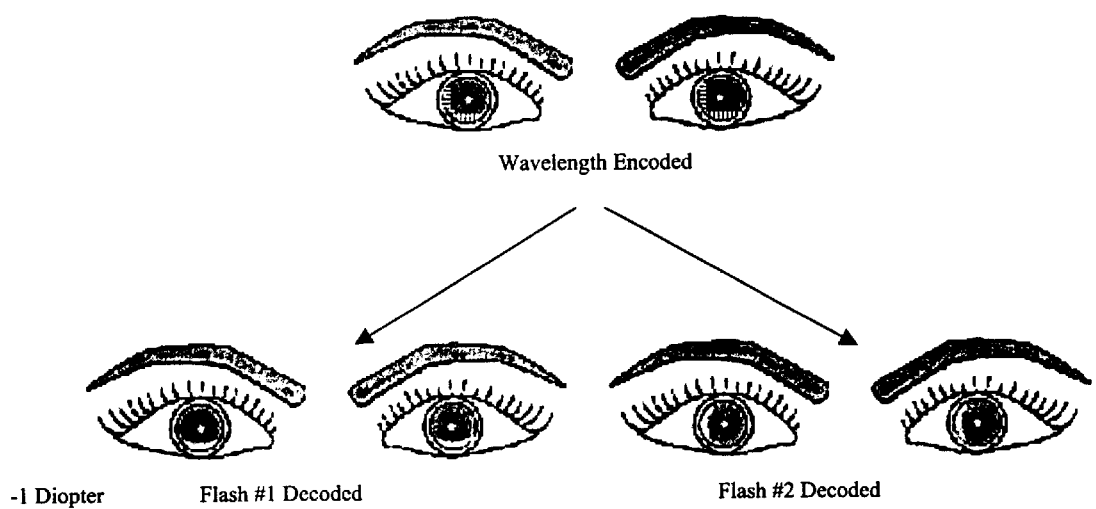
FIG. 13 is a figure showing an encoded image and a decoded pair of images of a patient's eyes indicating −1.0 diopters of myopia (nearsightedness).
Figure 14:
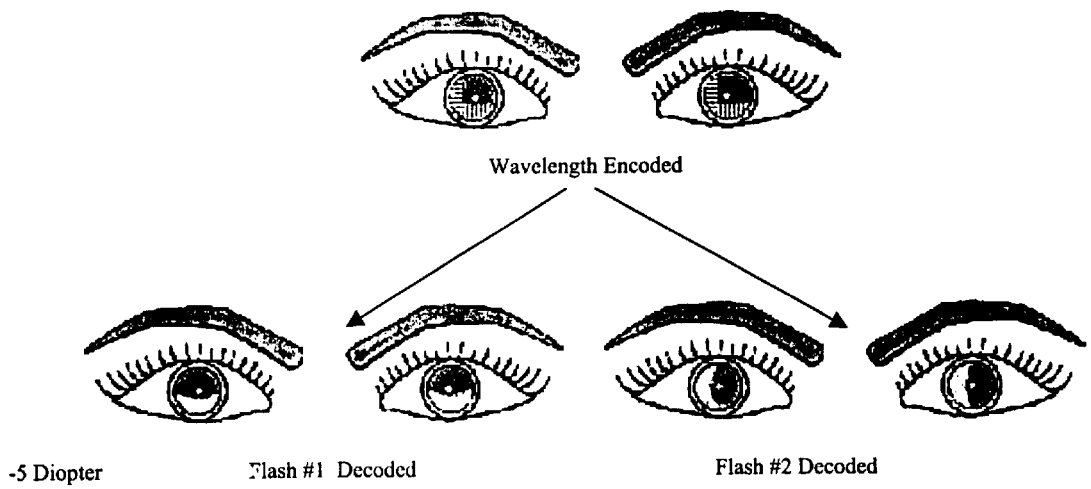
FIG. 14 is a figure showing an encoded image and a decoded pair of images of a patient's eyes indicating −5.0 diopters of myopia

FIG. 13 shows a patient's eyes indicating approximately −1.0 diopters of myopia (nearsightedness) and FIG. 14 shows approximately −5.0 diopters of myopia. Note that the crescents shown in the figures are much higher in the −5.0 diopter patient as compared to the −1.0 diopter patient. The appearance of the crescents in the images of the patient's eyes is caused by defocusing of the light source 12 on the retina of the patient's eyes and the more defocusing (i.e., the worse the vision), the higher the crescent.

Figure 15:
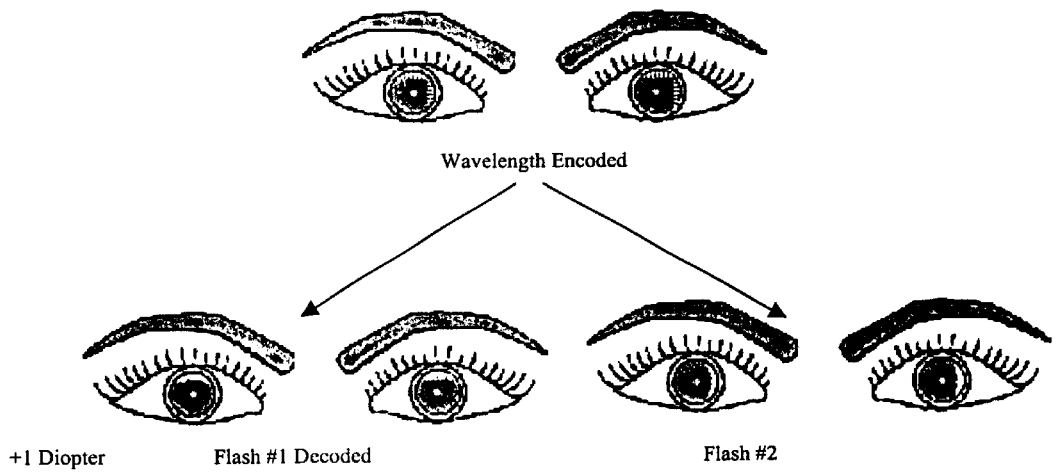
FIG. 15 is figure showing an encoded image and a decoded pair of images of a patient's eyes indicating +1.0 diopters of hyperopia (farsightedness).
Figure 16:
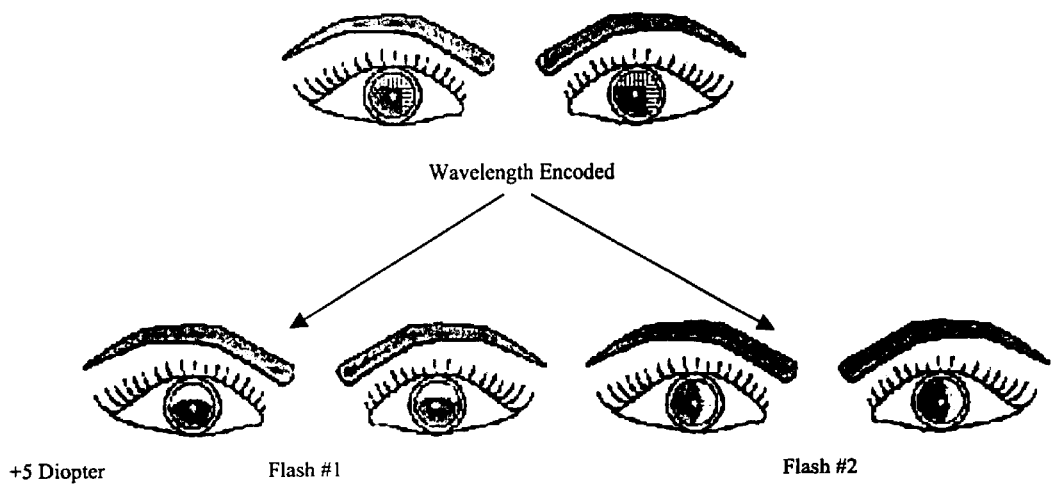
FIG. 16 is a figure showing an encoded image and a decoded pair of images of a patient's eyes indicating +5.0 diopters of hyperopia.

FIGS. 15 and 16 show a patient's eyes indicating approximately +1.0 diopters and +5.0 diopters of hyperopia (farsightedness), respectively. Note that these images are similar to the images shown in FIGS. 13 and 14 except that the crescents appear on the opposite side of the patient's eyes.

Figure 17:
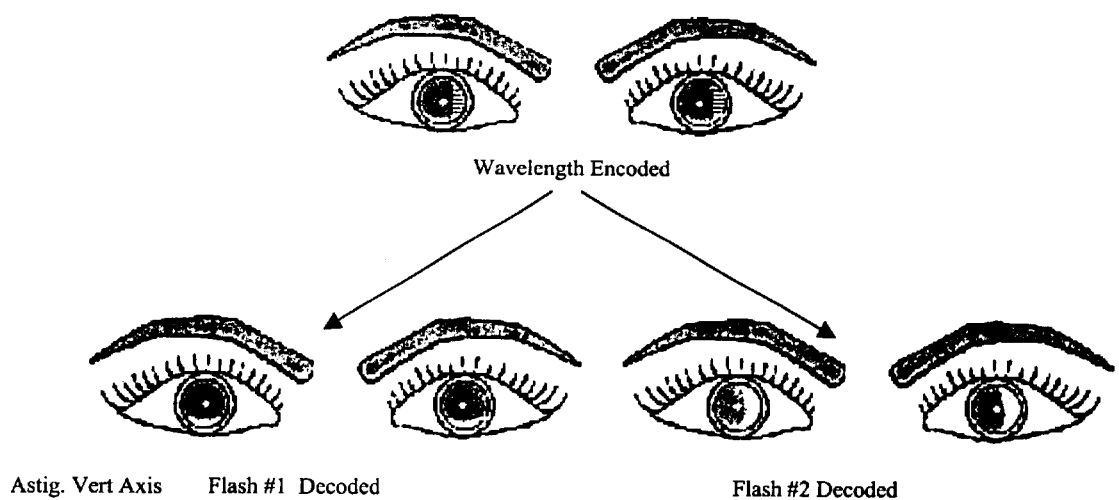
FIG. 17 is a drawing showing an encoded image and a decoded patient's eyes indicating astigmatism (cylinder optical power oriented vertically).
Figure 18:
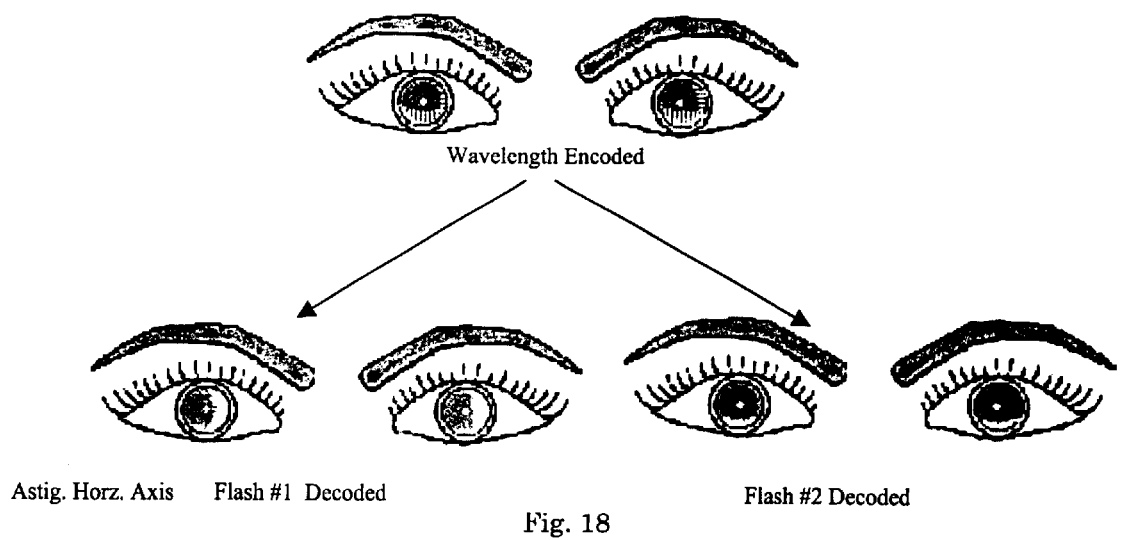
FIG. 18 is a drawing showing an encoded image and a decoded patient's eyes indicating astigmatism (cylinder optical power oriented horizontally).

Finally, FIGS. 17 and 18 show a patient's eyes indicating astigmatism (cylinder optical power) oriented vertically and horizontally, respectively.

As was the case with the analysis to detect cataracts, strabismus, and pupil size, the analysis to detect refractive errors may be performed manually (by a person reviewing the infrared images of the patient's eyes) or by using a computer. In one embodiment of the present invention, the computer 22 is operable to analyze the wavelength-decoded images to determine these conditions. In this embodiment, the computer system 22 analyzes the wavelength-decoded images by performing the following steps.

Referring again to FIG. 11, the computer system 22, using the pupil center calculated using the infrared image, defines a line along the center of the pupil in the first visible light image (i.e., the image obtained using the flash located on the side of the camera's objective lens) that is approximately 5 pixels wide and equal in length to the horizontal diameter of the pupil. Next, the computer system 22 calculates the degree of slope in this line.

The computer system 22 then defines a line along the center of the pupil in the second visible light image (i.e., the image obtained using the flash located below the camera's objective lens) that is approximately 5 pixels wide and equal in length to the vertical diameter of the pupil calculated using the infrared image of the eye. The computer system 22 then calculates the degree of slope in this line.

In both cases, the degree of slope is calculated by comparing the intensity of pixels along the line. If the pixels are all equally illuminated, then the slope of the line is zero. If, on the other hand, the pixels have different amounts of illumination, then the slope is non-zero, i.e., either positive or negative. In addition, if the absolute value of the slope is below a predetermined threshold value, then the computer system 22 determines that the patient does not have any significant refractive errors.

Finally, the computer system 22 compares the degree of slope in each image to determine if a patient is myopic, hyperopic, or has some degree of astigmatism. If the slopes are both positive and equal, then the computer system 22 determines that the patient is myopic. If, on the other hand, the slopes are both negative and equal, then the computer system 22 determines that the patient is hyperopic. If the slopes are unequal, the computer system 22 determines that the patient has some degree of astigmatism. The degree of astigmatism is determined by the ratio of the two slopes, the higher the ratio, the higher the degree of astigmatism.

Figure 19:
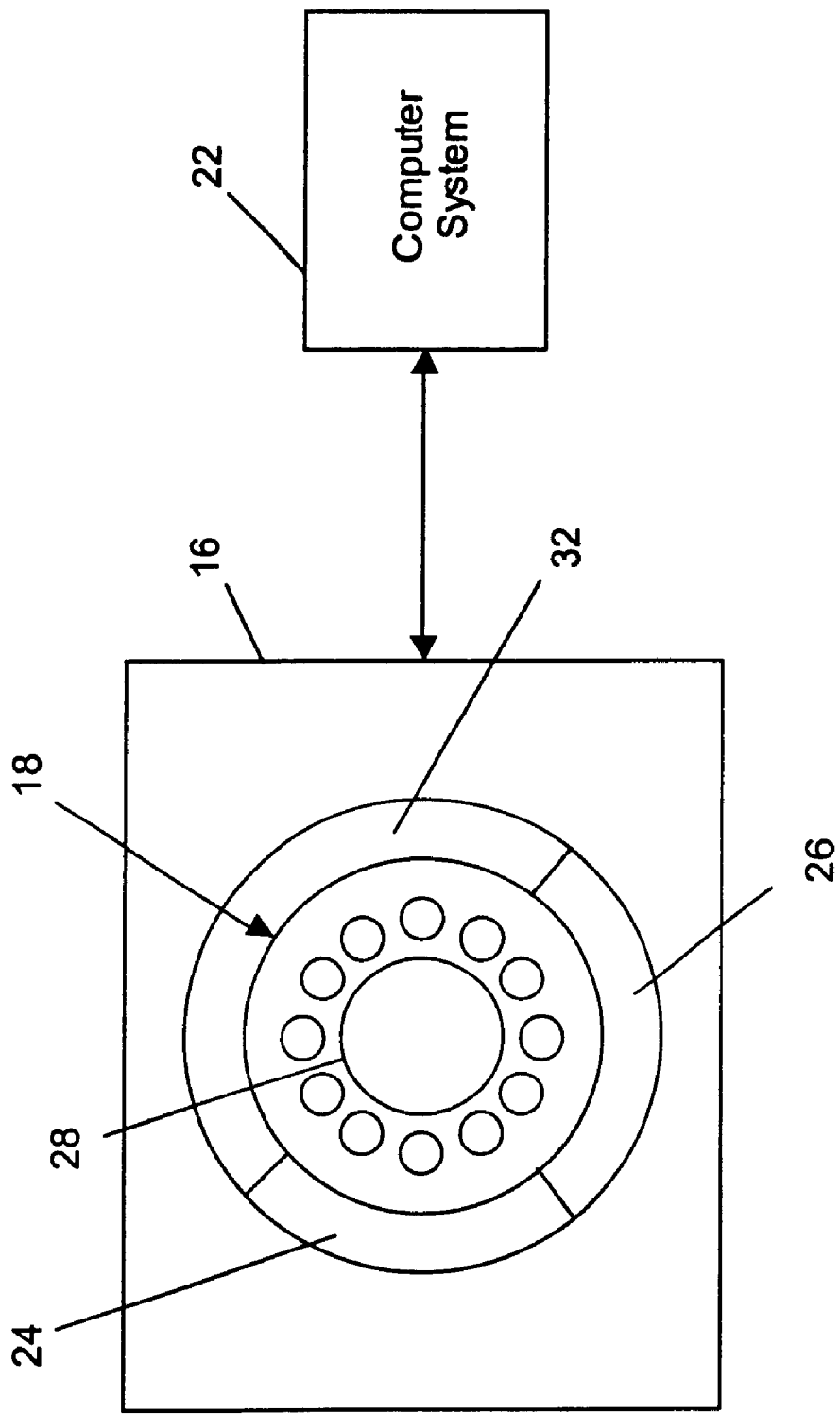
FIG. 19 is sketch diagram of a third embodiment of the present invention.

In an alternative embodiment, the two separate flashes 20 shown in FIG. 2 may be replaced by a single ring flash 30 (See FIG. 19). In this embodiment, filters 24 and 26 are the same as previously described with respect to FIG. 2 and the invention further includes an additional filter 32, which covers the portion of the ring flash 30 not covered by filters 24 and 26 and effectively blocks any light emitted by this portion of the ring flash 30. This embodiment only requires a single triggering circuit (not shown) for the ring flash 30 and thus requires less circuitry than the embodiment shown in FIG. 2., which requires two triggering circuits (not shown) for the two separate flashes 20.

Figure 21:
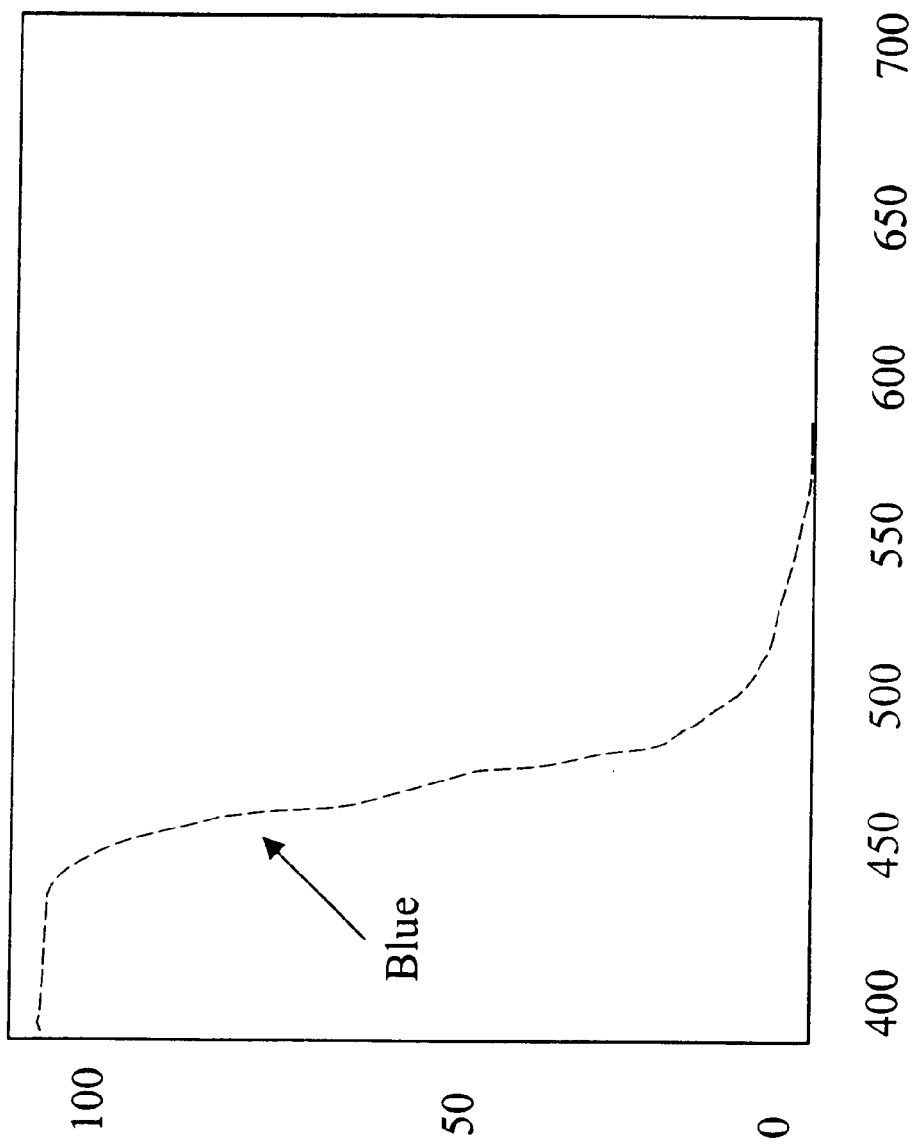
FIG. 21 is a plot showing the filter characteristics of a third wavelength-encoded filter used in the present invention.
Figure 22:
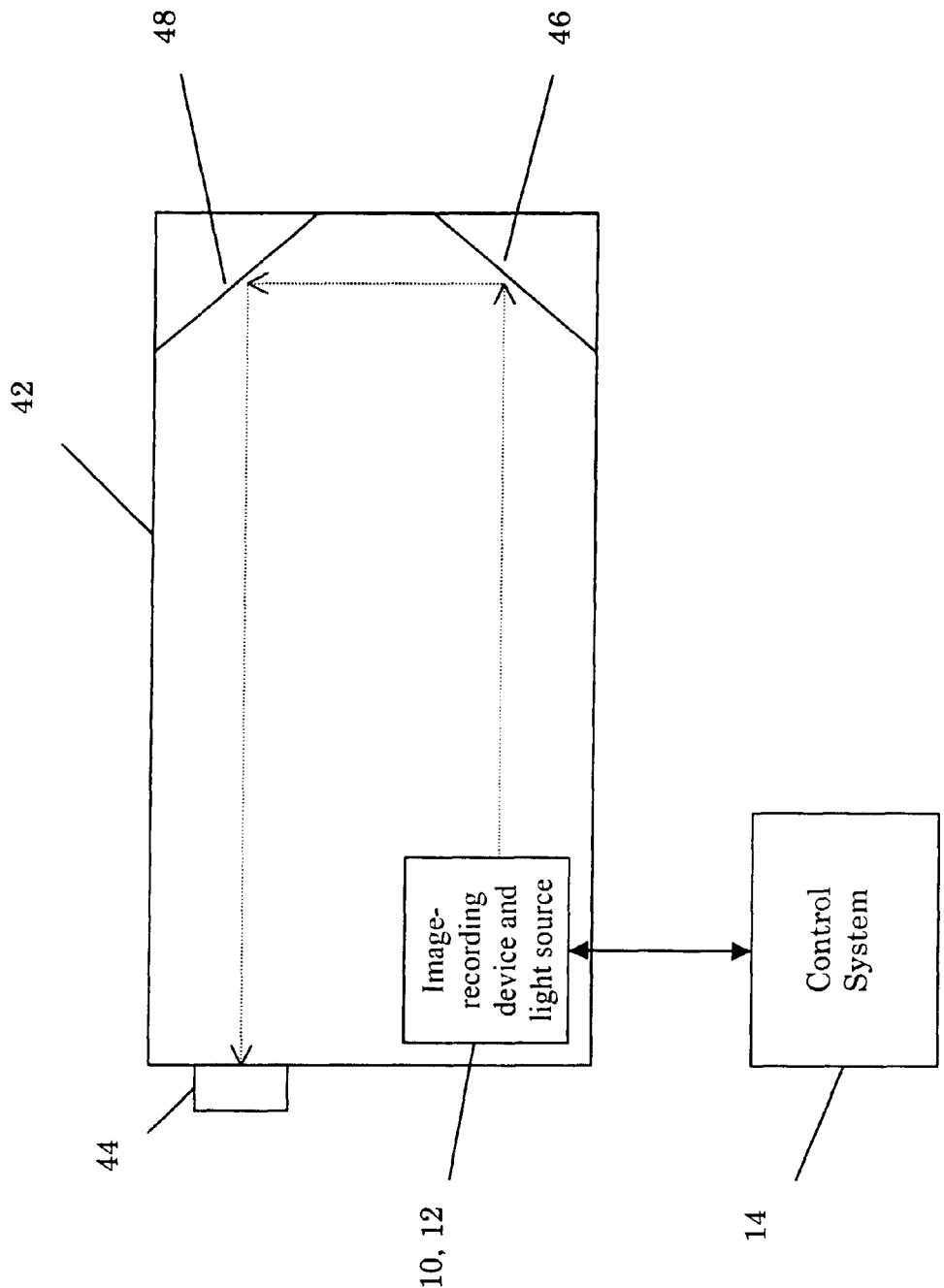
FIG. 22 is a drawing of a fifth embodiment of the present invention.

In still another alternative embodiment (see FIG. 20), the wavelength-encoded light source 12 includes an additional wavelength-encoded flash 34, which replaces the plurality of infrared LEDs, located in front of and above the axis 40 of the objective lens 28. Flash 34 includes a wavelength-encoded filter 36 for filtering out light having wavelengths outside of the range of wavelengths commonly referred to as the color blue. As a result, when the flash 34 is triggered, filter 36 emits blue light. The characteristics of filter 34 are shown in FIG. 21. As shown in FIG. 22, filter 36 only passes light having wavelengths ranging from approximately 400 nanometers to approximately 550 nanometers.

In this embodiment, the flash 34 is used to flood the patient's eyes with blue light in order to detect non-refractive errors, such as cataracts, and to determine pupil size and baseline retinal reflectivity. Unlike the previous embodiment where the infrared images were used to make this determination prior to illuminating the patient's eyes with wavelength-encoded light, this embodiment requires the determination to be made after the patient's eyes have been illuminated with the wavelength-encoded light. This is true because in this embodiment all of the flashes are triggered simultaneously and the image-recording device 10 is used to record a wavelength-encoded image while the patient's eyes are illuminated. The computer system 22 is then used to decode the resulting wavelength-encoded image into three separate wavelength-decoded images, which can be analyzed to identify non-refractive and refractive errors as discussed previously.

Figure 20:
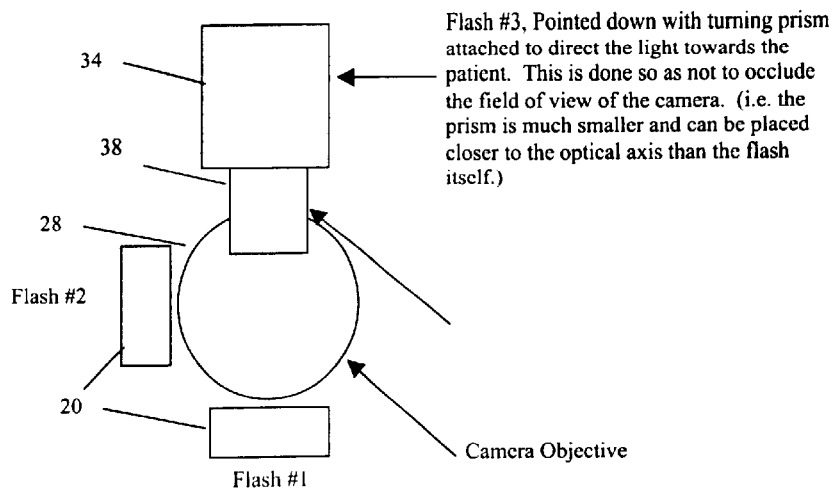
FIG. 20 is a sketch diagram of a fourth embodiment of the present invention.
Figure 20:
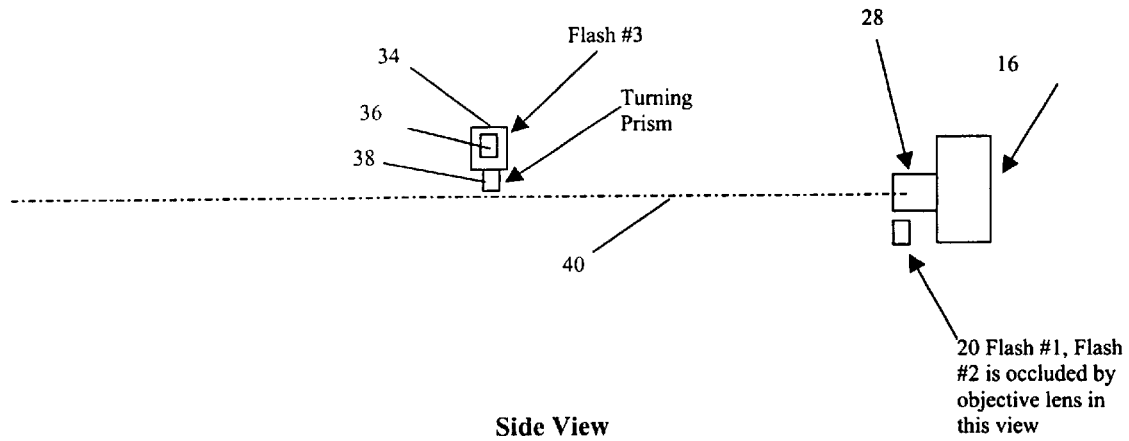

Since the flash 34 is large and, as a result, blocks some of the light reflected off of the patient's eyes, this embodiment also includes a small turning prism 38, which is connected to the flash 34 and positioned as close as possible to the optical axis 40 of the camera 16 (See FIG. 20). By using the small prism 38, it is possible to illuminate the patient's eyes while simultaneously reducing the amount of reflected light that is blocked.

Referring to FIG. 22, another embodiment of the present invention further includes an enclosure 42 designed to hold the image-recording device 10 and the light source 12. The enclosure 42 includes an opening (not shown), a headrest 44 positioned adjacent to the opening, a first mirror 46 positioned at a 45 degree angle with respect to the headrest 44, and a second mirror 48 positioned at a 45 degree angle with respect to the image-recording device 10 and light source 12.

In this embodiment, the infrared and visible light generated by the light source 12 is reflected from the first mirror 46 to the second mirror 48 and from the second mirror 48 through the opening in the enclosure and the headrest 44. Using the headrest 44, a patient's eyes may be positioned adjacent to the opening in the enclosure so that the eyes are illuminated by light passing out of the enclosure 42.

Although this embodiment includes a pair of mirrors positioned at 45-degree angles, other embodiments might exclude these mirrors. In such an embodiment, the image-recording device 10 and light source 12 would be positioned at one end of the enclosure, and the opening in the enclosure and the headrest would be positioned at the opposite end of the enclosure. By using mirrors, however, it is possible to use a smaller length enclosure and still maintain an optical path that is actually longer than the length of the enclosure.

Thus, although there have been described particular embodiments of the present invention of a new and useful Simultaneous, Wavelength Multiplexed Vision Screener, it is not intended that such references be construed as limitations upon the scope of this invention except as set forth in the following claims.

The invention claimed is:

1. An apparatus for detecting errors in a patient's eyes, comprising:
   a light source for illuminating at least two different meridians of the patient's eyes with wavelength-encoded light; and
   an image-recording device for recording a wavelength-encoded image of the eyes while illuminated by the wavelength-encoded light.

2. The apparatus of claim 1, wherein the image-recording device comprises a digital camera.

3. The apparatus of claim 2, wherein the light source comprises a pair of wavelength-encoded flashes positioned in two different meridians of the digital camera's optical axis.

4. The apparatus of claim 3, wherein:
   the light source includes a third wavelength-encoded flash for illuminating the eyes with blue light; and
   the image-recording device is operable to record an image of the eyes while illuminated with the blue light.

5. The apparatus of claim 2, wherein the light source comprises a wavelength-encoded ring flash.

6. The apparatus of claim 1, wherein:
   the light source includes an infrared light source for illuminating the eyes with infrared light; and
   the image-recording device is operable to record an image of the eyes while illuminated with infrared light.

7. The apparatus of claim 6, further comprising a control system for causing the infrared light source to illuminate the eyes and for causing the image-recording device to record an image of the eyes while illuminated by infrared light.

8. The apparatus of claim 7, wherein the control system is further operable to analyze the infrared image to determine pupil size.

9. The apparatus of claim 8, wherein the control system is further operable to analyze the infrared image to identify non-refractive errors in the eyes.

10. The apparatus of claim 1, further comprising a control system for causing the light source to simultaneously illuminate the eyes in at least two different meridians of the eyes using wavelength-encoded light and causing the image-recording device to record a wavelength-encoded image of the eyes while illuminated by the wavelength-encoded light.

11. The apparatus of claim 10, wherein the control system is further operable to decode the wavelength-encoded image into wavelength-decoded images and to analyze the wavelength-decoded images of the eyes to detect refractive errors in the eyes.

12. A method for detecting errors in a patient's eyes, comprising the steps of:
   simultaneously illuminating at least two different meridians of the eyes using wavelength-encoded light; and
   recording a wavelength-encoded image of the eyes while illuminated with the wavelength-encoded light.

13. The method of claim 12, further comprising the steps of:
   illuminating the eyes with infrared light;
   recording an infrared image of the eyes while illuminated by the infrared light; and
   identifying non-refractive errors, such as media opacities or strabismus, in the eyes using the recorded infrared image.

14. The method of claim 13, further comprising the step of analyzing the infrared image to identify physical characteristics of the eyes.

15. The method of claim 14, wherein the step of identifying physical characteristics comprises the step of identifying pupil size.

16. The method of claim 14, wherein the step of identifying physical characteristics comprises the step of identifying eye gaze angle.

17. The method of claim 12, further comprising the step of decoding the wavelength-encoded image into wavelength-decoded images and analyzing the wavelength-decoded images to identity refractive errors in the eyes.

18. An apparatus for generating images of eyes for use in identifying non-refractive and refractive errors, comprising:
   a camera having an objective lens;
   an infrared light source located coaxially with the camera's objective lens;
   a first flash positioned adjacent to the infrared light source and operable to emit a first color of light in a first meridian around the objective lens; and
   a second flash positioned adjacent to the infrared light source and operable to emit a second color of light in a second meridian around the objective lens.

19. The apparatus of claim 18, wherein the camera comprises a color digital camera.

20. The apparatus of claim 18, wherein the camera comprises a conventional film camera.

21. The apparatus of claim 18, wherein the infrared light source comprises a plurality of infrared LEDs.

22. The apparatus of claim 18, wherein the first color of light matches the red response of a Red-Green-Blue color camera and the second color matches the green response of a Red-Green-Blue color camera.

23. The apparatus of claim 18, wherein the first flash is positioned approximately 90 degrees from the second flash.

24. An apparatus for generating images of eyes using infrared and visible light, comprising:
   a camera having an objective lens;
   an infrared light source located coaxially with the objective lens;
   a ring flash encircling the infrared light source, the ring flash operable to emit a first color of light in a first meridian around the objective lens and to emit a second color of light in a second meridian around the objective lens.

25. The apparatus of claim 24, wherein the camera comprises a color digital camera.

26. The apparatus of claim 24, wherein the camera comprises a conventional film camera.

27. The apparatus of claim 24, wherein the infrared light source comprises a plurality of infrared LEDs.

28. The apparatus of claim 24, wherein the first color of light matches the red response of a Red-Green-Blue color camera and the second color matches the green response of a Red-Green-Blue color camera.

29. A system for generating infrared and wavelength-encoded images of eyes, comprising:
   a camera having an objective lens;
   an infrared light source located coaxially with the objective lens;
   a first flash positioned adjacent to the infrared light source and operable to emit a first color of light in a first meridian around the objective lens; and
   a second flash positioned adjacent to the infrared light source and operable to emit a second color of light in a second meridian around the objective lens; and
   a control system, in communication with the camera, infrared light source, and flashes, operable to cause the infrared light source to emit infrared light and to cause the camera to capture an infrared image of the eyes using the emitted infrared light, the control system further operable to cause the flashes to fire simultaneously and to cause the camera to capture a wavelength-encoded image of the eyes using the light emitted by the flashes.

30. The apparatus of claim 29, wherein the camera comprises a color digital camera.

31. The apparatus of claim 29, wherein the camera comprises a conventional film camera.

32. The apparatus of claim 29, wherein the infrared light source comprises a plurality of infrared LEDs.

33. The apparatus of claim 29, wherein the first color of light matches the red response of a Red-Green-Blue color camera and the second color matches the green response of a Red-Green-Blue color camera.

34. The apparatus of claim 29, wherein the first flash is positioned approximately 90 degrees from the second flash.

35. The apparatus of claim 29, wherein the control system comprises a computer system having a monitor for displaying the infrared and wavelength-encoded images.

36. A system for identifying non-refractive and refractive errors in eyes, comprising:
   a camera having an objective lens;
   an infrared light source located coaxially with the objective lens;
   a first flash positioned adjacent to the infrared light source and operable to emit a first color of light in a first meridian around the objective lens; and
   a second flash positioned adjacent to the infrared light source and operable to emit a second color of light in a second meridian around the objective lens; and
   a control system, in communication with the camera, infrared light source, and flashes, operable to cause the camera to record an infrared image of the eyes while illuminated by infrared light and a wavelength-encoded image of the eyes while illuminated with wavelength-encoded light, the control system further operable to process the infrared image to identify non-refractive errors in the eyes and to process the wavelength-encoded image to identify refractive errors in the eyes.

37. The system of claim 36, wherein:
   the non-refractive errors include media opacities or strabismus, and
   the refractive errors include myopia, hyperopia, or astigmatism.

38. The system of claim 37, wherein the control system identifies media opacities based on the amount of infrared light reflected by the pupil of the eye.

39. The system of claim 37, wherein the control system identifies strabismus by calculating the gaze angle of the eye using the infrared image.

40. The system of claim 36, wherein the control system calculates the pupil diameter of the eyes using the infrared image.

41. The system of claim 36, wherein the control system decodes the wavelength-encoded image into a pair of wavelength-decoded images and processes the wavelength-decoded images to identify refractive errors.

42. The system of claim 41, wherein the control system identifies refractive errors by measuring the amount and distribution of wavelength-encoded light reflected by the pupil of the eye.

43. A method for identifying errors in eyes, comprising the steps of:
   generating an infrared image of the eyes;
   identifying non-refractive errors using the infrared image;
   generating a wavelength-encoded image of the eyes;
   decoding the wavelength-encoded image of the eyes into wavelength-decoded images; and
   identifying refractive errors using the wavelength-decoded images.

44. The method of claim 43, further comprising the step of determining pupil diameter.

45. The method of claim 43, wherein the step of identifying non-refractive errors comprises the step of identifying media opacities or strabismus.

46. The method of claim 45, wherein the step of identifying media opacities includes the steps of measuring the mean amount of infrared light reflected by the pupil of the eye and comparing the mean amount to the actual amount reflected by the pupil of the eye on a pixel by pixel basis.

47. The method of claim 45, wherein the step of identifying strabismus includes the step of measuring eye gaze angle.

48. The method of claim 43, wherein the step of identifying refractive errors comprises the step of identifying myopia, hyperopia, or astigmatism.

49. The method of claim 48, wherein the step of identifying myopia, hyperopia, or astigmatism includes the step of measuring the distribution of light reflected by the pupil of the eye on each wavelength decoded image.

50. The method of claim 48, wherein the step of identifying myopia, hyperopia, or astigmatism includes the steps of defining a line through each pupil of the eye, calculating the slope of each line, and comparing the slopes of each line.

\* \* \* \* \*